(12) United States Patent
Boebel et al.

(10) Patent No.: US 8,545,448 B2
(45) Date of Patent: Oct. 1, 2013

(54) TROCAR SLEEVE

(75) Inventors: Manfred Boebel, Bauschlott (DE);
Ludwig Bonnet, Knittlingen (DE);
Eberhard Koerner, Knittlingen (DE);
Roland Raakow, Berlin (DE); Georg Liesaus, Potsdam (DE)

(73) Assignee: Richard Wolf GmbH, Knittlingen (DE)

(*) Notice: Subject to any disclaimer, the term of this patent is extended or adjusted under 35 U.S.C. 154(b) by 0 days.

(21) Appl. No.: 12/974,639

(22) Filed: Dec. 21, 2010

(65) Prior Publication Data
US 2011/0160672 A1    Jun. 30, 2011

(30) Foreign Application Priority Data

Dec. 24, 2009 (DE) .......... 10 2009 060 377

(51) Int. Cl.
*A61M 5/178* (2006.01)
(52) U.S. Cl.
USPC ............................................. 604/164.01
(58) Field of Classification Search
USPC ........... 604/164.1, 164.11, 164.01–164.09, 604/167.01–167.06; 606/108, 185
See application file for complete search history.

(56) References Cited

U.S. PATENT DOCUMENTS

| 5,258,003 | A | 11/1993 | Ciaglia et al. |
| 5,271,414 | A | 12/1993 | Partika et al. |
| 5,662,673 | A | 9/1997 | Kieturakis |
| 5,735,867 | A | 4/1998 | Golser et al. |
| 6,517,519 | B1 * | 2/2003 | Rosen et al. ............ 604/164.06 |
| 6,551,270 | B1 | 4/2003 | Bimbo et al. |
| 7,092,765 | B2 | 8/2006 | Geske et al. |
| 7,470,230 | B2 * | 12/2008 | Smith et al. .................. 600/184 |
| 2005/0203565 | A1 | 9/2005 | Rethy et al. |
| 2008/0255519 | A1 | 10/2008 | Piskun et al. |
| 2009/0036738 | A1 | 2/2009 | Cuschieri et al. |

FOREIGN PATENT DOCUMENTS

| DE | 10 2005 026 467 A1 | 12/2006 |
| DE | 60 2004 005 116 T2 | 10/2007 |
| DE | 603 11 487 T2 | 10/2007 |
| JP | 07-21004 U | 4/1995 |

OTHER PUBLICATIONS

Office Action Issued Aug. 3, 2010 in German Appln. Ser. No. 10 2009 060 377.8.
Office Action issued Sep. 26, 2012 in CN Application No. 201010621087.6.
Office Action issued Oct. 23, 2012 in JP Application No. 2010-288357.

* cited by examiner

*Primary Examiner* — Jason Flick
(74) *Attorney, Agent, or Firm* — Panitch Schwarze Belisario & Nadel LLP

(57) ABSTRACT

A trocar sleeve includes a distal tubular section, a section which connects to the distal tubular section at a proximal side of the distal tubular section and which is widened proximally, and at least one spiral with a circular outer contour, arranged helically on a periphery of the distal tubular section. The distal tubular section includes a rounded polygonal cross section so that maximal degrees of freedom of the applied instruments result.

12 Claims, 2 Drawing Sheets

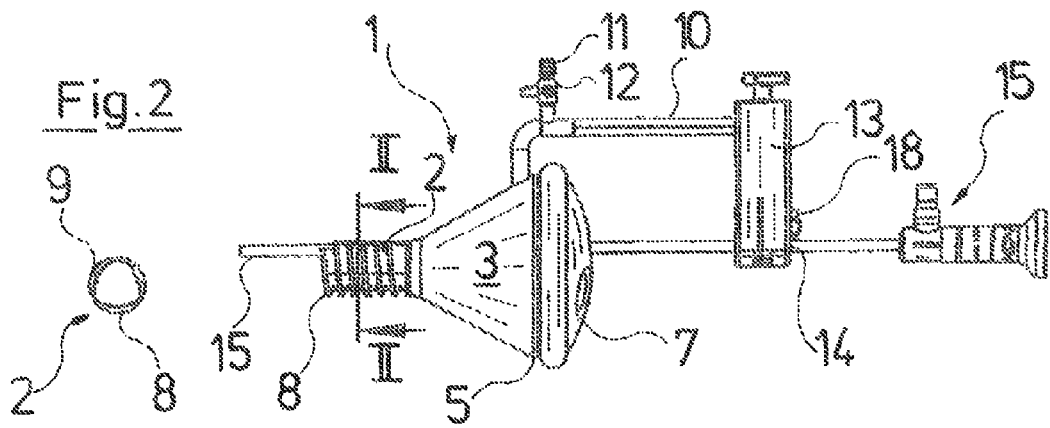
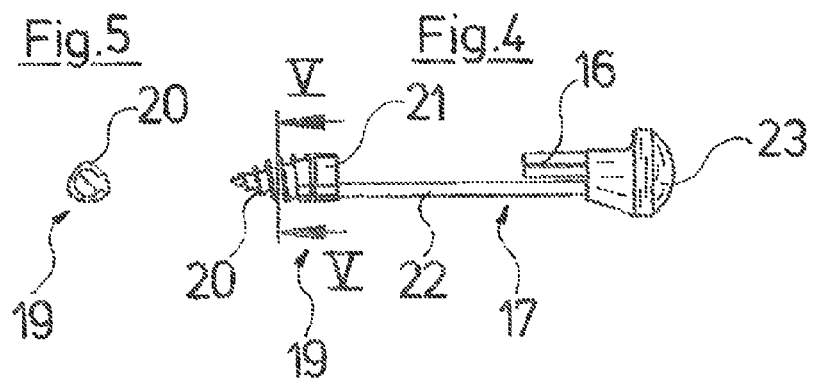

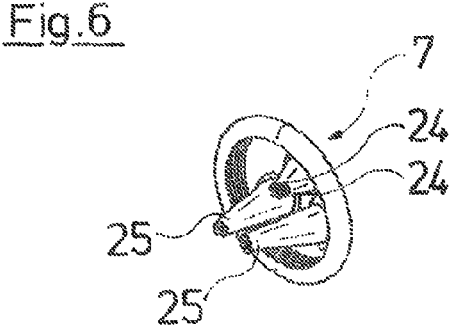
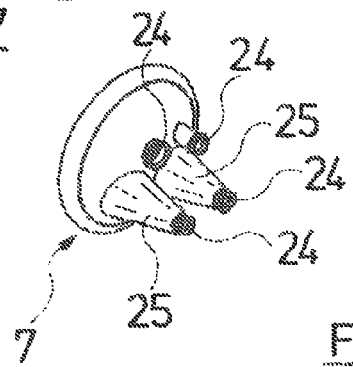
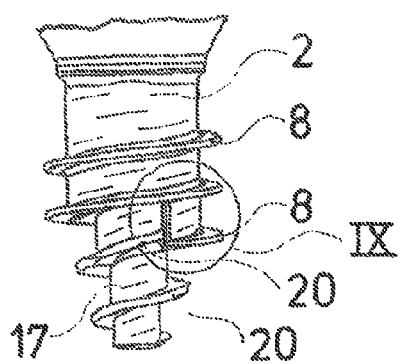
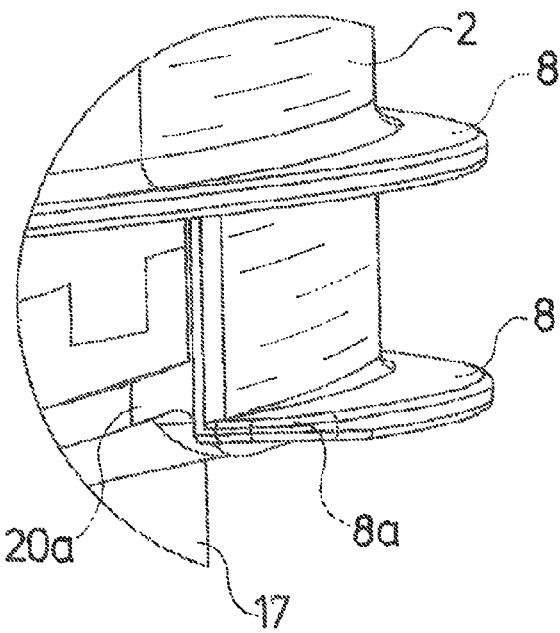

TROCAR SLEEVE

BACKGROUND OF THE INVENTION

The present invention relates to a trocar sleeve, as well as further to the associated trocar.

A trocar is an instrument, with whose help one creates an access to a body cavity in particular the abdominal cavity, with minimal evasive surgery. A trocar sleeve which is inserted together with the trocar and which holds open the later access into the body cavity, belongs to the trocar. The trocar together with the trocar sleeve is introduced, for example, through the abdominal wall, whereupon the trocar is pulled out and the introduction of instruments such as optical tools, gripper tools, cutter tools or other tools may be effected via the remaining trocar sleeve.

In order to fasten the trocar sleeve, for example, in the abdominal wall, it is counted as belonging to the state of the art to provide this with a suitable thread, for example, with a spiral arranged in a helical manner, at the distal end. Such trocar sleeves are known from U.S. Patent Application Publication No. 2008/0255519 A1 (Picksun). In Picksun, a trocar sleeve is particularly described by way of FIGS. 24 and 25, whose distal end section on the outer side is provided with a spiral and which at the proximal side, merges into region widened in a funnel-like manner. The trocar sleeve is to be reliably fastened in the wall of the body cavity, e.g., the abdominal wall, amid the compression of this, by way of the thread. The instruments thereby are to be introduced through the comparatively narrow cylindrical inner cross section, and a guide in the distal end section is provided there for a laparoscope or endoscope optics, but this guide however additionally limits the remaining cross section and thus additionally makes the introduction of further instruments more difficult. The trocar sleeve of Picksun is also not suitable for receiving a trocar.

A trocar sleeve in the form of a conical insert is known from German Publication No. 10 2005 026 467 A1 (Cuschieri), and comprises a spiral on the outer periphery and a guide for an instrument on the inner side. Since the guide is arranged parallel to the conical wall, the instrument may only be introduced and held, in this direction. Although the circular free space formed at the distal end, for the passage into the body cavity, is largely free of the guide due to the oblique leading, however the arrangement parallel to the wall necessitates an oblique guiding of the instrument, by which means the access is practically likewise narrowed. The conical outer side with the spiral arranged thereon furthermore does not provide for a sufficient grip, since a compression of the abdominal wall with this arrangement may not be effected and thus a more secure grip is not guaranteed.

BRIEF SUMMARY OF THE INVENTION

Against this background, it is an object of the present invention to provide a trocar sleeve, which does not have the above-described disadvantages and, with a comparatively small cross section, ensures an improved access for instruments as well as an improved retention in the introduced body opening.

The above object is achieved by a trocar sleeve comprising a distal, tubular section and a section which connects thereto at the proximal side and which is widened proximally. Here at least one helically arranged spiral, which has a circular outer contour seen in the direction of the longitudinal axis of the trocar sleeve, is provided on the periphery of the distal tube section. According to the present invention, the tube section has a rounded polygonal cross section.

Thus, it is the basic concept of the present invention not to provide the tubular section which penetrates into the body and is typically anchored in the abdominal wall, with a circular cross section, as is otherwise commonplace, but with a rounded polygonal cross section. A rounded polygonal cross section is to be understood as one which is polygonal per se, but with which adjacent sides of the profile are not designed as a corner, but as a rounding. The distal tubular section is formed in a manner known per se by a comparatively thin-walled tube, wherein the tube cross section is not designed in a circular or oval manner as is usual, but in a polygonal manner. Thereby, however, only this distal tubular section is designed in this shape, and the surrounding helically arranged spiral however has a circular outer contour.

This design according to a preferred embodiment of the present invention is particularly advantageous, since, given the same cross-sectional area, a polygonal cross section is more favourable than a circular cross section with regard to the arrangement and the movement ability of the instruments to be led through. The pivoting ability of the instruments, thus their ability to be set obliquely with respect to the longitudinal axis of the trocar sleeve, is significantly improved and moreover the instruments mutually inhibit one another only to a limited extent. A further significant advantage is the support surface of the spiral which is larger compared to the state of the art, via which the body tissue, thus in particular the abdominal wall may be accommodated and thus the trocar sleeve fixed. Since differently effective widths of the spiral result due to the round outer contour and the polygonal tube cross section, the spiral sections lying parallel to the sides of the polygon may be designed wider than with a circular inner tube with comparable dimensions, by which means and improved compression of the abdominal wall and a more secure grip of the trocar sleeve within the abdominal wall may be achieved.

Usefully, the spiral or spirals are connected over their whole length in a distance-free manner on the outer periphery of the distal tube section, so that the spiral forms a type of outer thread with a changing flank width.

It has been found to be particularly advantageous to provide the distal tube section with a rounded, triangular cross section, thus in a manner such that flat tube walls which are typically but not necessarily arranged at an angle of 120° to one another, are formed, which by way of suitably rounded sections are connected into a tube, in a manner such that the wall thickness of the tube is constant over the periphery as well as over the length, and a continuous cross-sectional course results, as is typically useful for the creation of a gas-tight access, e.g., via the navel. Thereby, the rounded, triangular cross section of the tubular section on the one hand results in maximal degrees of freedom for the auxiliary instruments which are guided therethrough and, on the other hand, also results in maximal support surfaces of the spiral or spirals, specifically where these connect to the sides of the triangle cross section.

In order, after the creation of the access and the removal of the trocar, to be able to maintain the pneumoperitoneum which is typically built up with such operations, according to a further formation of the present invention, means for the releasable or pivotable attachment of sealing means, in particular a sealing cap, are provided on the proximal side, and these means seal the trocar sleeve to the outside on the proximal side and comprise at least one opening for leading through an instrument, said opening closing or being able to be closed in an automatic manner. This seal is advantageously attached in a releasable or pivotable manner, so that it is not a hindrance on introducing or removing the trocar, and on the other hand so that it may be adapted to the respective instrument set as the case may be and is exchangeable, as well as for hygienic reasons, so that, as the case may be, it may be provided packaged in a sterile manner as a disposable article Advantageously, this may be realised in that, according to a further formation of the present invention, an end section is provided on the widened section of the trocar sleeve on the proximal side, said end section being provided with a peripheral bead, over which the sealing cap engages. The engagement of the sealing cap over the bead has several advantages with regard to application technology. On the one hand, such a seal is quick and simple to attach and remove by the user. Moreover, the sealing cap grips over the proximal edge of the trocar sleeve, by which means injuries in the region of this edge, as occasionally occur with funnel-like trocars of this type, may be avoided or at least reduced. The peripheral bead, which holds the sealing cap on the trocar sleeve, may be formed by grooving a groove or also by way of integrally forming onto the proximal-side end section. The groove arrangement moreover has the advantage that the sealing effect is not only achieved by way of the engagement over the bead, but by way of the bearing of the engaging-over cap edge in the groove, and moreover the sealing cap is held better.

Moreover, the proximal end section may advantageously be provided for the attachment of, for example, a rod-like holder which connects radially to the outer side of the end section, is bent by about 90° at a small distance thereto and is then led proximally, parallel to the longitudinal axis of the trocar sleeve. Advantageously, a holding arm is arranged in an adjustable manner on this holder and is designed for guiding and fixing an instrument which is led through the trocar sleeve. Usefully, this holding arm serves for guiding and fixing endoscope optics, but may however also be used basically for fixing other instruments. The holding arm may however serve also for the fixation of the trocar in the trocar sleeve, which is particularly advantageous.

If, as is envisaged in a further formation of the present invention, the holding rod is designed hollow at least in sections, then a conduit connection into the inside of the trocar sleeve may be formed via this, if a corresponding and preferably shuttable conduit connection is provided on the holding rod or at least branches from this. The pneuoperitoneum is supported or built up via such a conduit connection.

It is particularly advantageous if the present inventive and previously described trocar sleeve is provided with a trocar, which as is known per se, may be fixed within the trocar sleeve and which comprises an end section which tapers distally into a tip. According to a further formation of the present invention, the outer contour of the trocar, in particular in the widest region of the tapered end section, is adapted to the outer contour of the inner cross section of the distal tube section of the trocar sleeve which in this region on an outer side is provided with at least one spiral. Thereby, this end section tapered into a tip also comprises a number of spirals which corresponds to that of the distal tube section, which are likewise arranged rising proximally from the tip in a helical manner, and the flush or proximally displaced spirals connect on the periphery of the distal tube section, when the trocar is fixed in the trocar sleeve in the correct position for creating an access through the abdominal wall. Thereby, analogously to the spiral arrangement and the cross-sectional shape in the region of the distal end section, it is particularly useful if the trocar, in the region of its end section which is tapered towards the tip, has a circular cross section, thus a conical shape, whereas the spiral or spirals in their width is or are formed corresponding to the inner contour of the surrounding distal tube section of the trocar sleeve. Then, in the region of the end section of the trocar which tapers into a tip, on the one hand a simple penetration into the body results, wherein a large support capability in this region is given on account of the at least sectional, comparatively wide spirals, and this support capability securely prevents the trocar from slipping away already after a small penetration. Moreover, the trocar with its end section tapering into a tip, in its correct introduction position, is advantageously arranged such that it does not completely penetrate the trocar sleeve, in particular in the region of the distal tube section, so that a positive fit between the proximal part of the this end section and the distal part of the distal tube section of the trocar sleeve is formed, so that a torque may be transmitted from the trocar sleeve onto the trocar, which is particularly advantageous for introduction.

Alternatively to the flush connection of the spiral of the trocar to the spiral of the trocar sleeve, the distal spiral end of the trocar sleeve is arranged slightly displaced distally, in order to prevent tissue from being able to get into the transition region of the spiral between the trocar and the trocar sleeve, on rotating the trocar sleeve into the abdominal wall.

The trocar itself is provided on the proximal side on the tapered end section with a rod which connects thereto and which comprises a handle on the end side, thus at the proximal end. Thereby, the rod is dimensioned such that the handle projects beyond the trocar sleeve on the proximal side, when the trocar is fixed in the trocar sleeve in its correct position (introduction position).

For fixing the trocar in the correct position, according to a further formation of the present invention, means for fastening the trocar preferably on the holding arm, are provided on the handle or on the rod. Since the holding arm is provided in any case for guiding and fastening instruments, with this, one may advantageously also fix the trocar on the trocar sleeve at least in the axis direction of this. In the rotation direction, the fastening results by way of the positive fit due to the polygonal cross-sectional shape. By way of this, one may also ensure that the spiral or spirals always connect in a flush manner from the distal end section of the trocar, to the spirals on the periphery of the distal tube section of the trocar sleeve.

In order to be able to fix the trocar in the trocar sleeve by way of the holding arm, a distally directed holding rod is advantageously provided on the handle parallel to the rod, and this holding rod is only half as long as the rod between the handle and the distal end section of the trocar and may be introduced into the holding arm and fixed there.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is a greatly simplified schematic representation of a trocar sleeve according to a preferred embodiment of the present invention, with inserted endoscope optics in a lateral view;

FIG. 2 is a sectional view taken along the section line II-II in FIG. 1;

FIG. 3 is a longitudinal sectional view of the trocar sleeve shown in FIG. 1, with a trocar inserted therein;

FIG. 4 is a lateral view of the trocar according to a preferred embodiment of the present invention;

FIG. 5 is a sectional view taken along the section line V-V in FIG. 4;

FIG. 6 is a perspective representation of a sealing cap shown in FIG. 1, seen from the inner side;

FIG. 7 is a perspective representation of the sealing cap in accordance with another preferred embodiment of the present invention;

FIG. 8 is a greatly enlarged lateral view of a distal end of the trocar sleeve with an inserted trocar; and FIG. 9 is an enlarged view of the detail IX in FIG. 8.

DETAILED DESCRIPTION OF THE INVENTION

Certain terminology is used in the following description for convenience only and is not limiting. The word "right" designates a direction in the drawings to which reference is made. The word "inwardly" refers to a directions toward a geometric center of the device, and designated parts thereof, in accordance with the present invention. Unless specifically set forth herein, the terms "a," "an" and "the" are not limited to one element, but instead should be read as meaning "at least one." The terminology includes the words noted above, derivatives thereof and words of similar import.

Referring to the drawings in detail, wherein like numerals indicate like elements throughout the several views, FIGS. 1-9 show a trocar sleeve 1 preferably including a distal tubular section 2, onto which a proximally widened section 3 connects on the proximal side (on the right side in FIG. 1), and this section 3, as the representations according to FIGS. 1 and 3 illustrate, is designed in a roughly truncated-cone-like manner and merges into the distal tube section 2 in a flush manner, so that the funnel-like shape evident from FIG. 2 results. On the proximal side, an end section 4 connects to the proximally widened section 3 of the trocar sleeve 1 and this end section 4 on the outer side continues the truncated-cone-shape of the section 3 up to a peripheral groove 5, onto which a bead 6 connects on the end side, said bead together with the groove 5 being provided for the releasable fastening of a sealing cap 7. The inner side of the end section 4 is designed in a cylindrical manner.

The distal tube section 2 preferably comprises a rounded triangular cross section, as is to be deduced from FIG. 2. This tube section 2 is provided with a helically peripheral spiral 8 which has an essentially circular outer contour, as may be deduced from FIG. 2. The spiral 8 connects at the inner side in a stepless manner to the outer periphery of the tube section 2, so that a larger spiral width results in the region of the sides 9 of the triangular cross section, than in the corner regions.

In the region of the end section 4, a holding rod 10 connects radially on the outer periphery, and this holding rod is bent up by 90° at a distance to the outer periphery and there runs proximal and parallel to the longitudinal axis of the trocar sleeve 1. The holding rod 10 in the region, in which it connects to the end section 4, is designed hollow on the inside, and is conductively connected to the inside of the trocar sleeve 1 via a corresponding recess in the end section 4. Directly behind the 90° bending, a conduit 11 is connected to the hollow region of the holding rod 10, in which conduit a shut-off valve 12 is seated and said conduit 11 being designed as a conduit connection at the free end behind the shut-off valve 12. The holding rod 10 in the further course is formed of solid material and has a hexagonal cross section. In this region, a holding arm 13 is displaceably guided on the holding rod 10 which at its free end comprises a receiver and a guide opening 14, in which an instrument e.g. the endoscope optics 15 represented in FIG. 1 or a holding rod 16 of a trocar 17, may be selectively fixed. The receiver and guide opening 14 run parallel to the longitudinal axis of the trocar sleeve and slightly offset to this. It comprises an eccentric lever 18, with which the instrument 15 or the holding rod 16 may be fixed in this.

The trocar 17 represented by way of FIGS. 4 and 5 comprises a distal end section 19 which tapers in a converging manner into a tip and which from this tip is firstly designed in a conically widened manner, where it is provided with a helically running spiral 20. As FIG. 5 illustrates, the conical part preferably comprises a round cross section, whereas the spiral 20 is designed and arranged such that seen in the axis direction of the trocar (FIG. 5), a triangularly rounded outer contour results, corresponding to the inner contour of the tube section 2 of the trocar sleeve 1. The spiral 20 runs out on the proximal side into a proximal part 21 of the end section 19, whose outer cross section corresponds to the inner cross section of the tube section 2 of the trocar sleeve 1 and which in this region may be provided with an O-ring for sealing. If the trocar 17 is seated in its correct position in the trocar sleeve 1 (see FIG. 3), then this proximal part 21 of the end section 19 is seated within the tube section 2. The spiral 20 then connects to the spiral 8 in a flush manner, which continues this, as is evident from FIG. 3.

Instead of a flush connection of the spiral ends which connect to one another, as is also represented by way of FIGS. 8 and 9, these may also connect axially displaced to one another by a small amount, for example corresponding to the spiral thickness. Thereby, the distal spiral end 8a of the trocar sleeve 1 connects distally, displaced by a small amount, to the proximal spiral end 20a of the spiral 20 of the trocar 17, as is clearly evident from FIG. 9.

Held in this position (FIG. 3), the end section 19 is held by a rod 22 which connects proximally thereto and which reaches up to a handle 23 at the proximal end of the trocar. The holding rod 16 which is provided for fastening in the receiver and the guide opening 14 of the holding arm 13, extends distally from the handle 23, parallel to the rod 22.

If the holding arm 13, which is displaceably guided on the holding rod 10, is located in the end position represented in FIG. 3, in which the holding arm 13 bears on the conduit 11 in an abutting manner and is fixed in this position, then the receiver and guide opening 14 are arranged such that with the insertion of the holding rod 16 so far, until the handle 23 bears on the proximal side of the holding arm 13, the position is reached, in which the trocar 17 is correctly arranged in the trocar sleeve 1, in order to be able to carry out its function as a trocar, thus for penetrating the abdominal wall in the navel region.

The trocar 17 may be removed by way of simply pulling out in the proximal direction, after the trocar 17 together with the trocar sleeve 1, as is represented in FIG. 3, is introduced and the distal tube section 2 with its spiral 8 is fixed in the abdominal wall amid the compression of this, whereupon the access to the body cavity is held open by way of the trocar sleeve.

The trocar sleeve 1 is sealed to the outside by way of attachment of the sealing cap 7 which is pushed over the bead 6, so that it engages into the groove 5 in a sealing manner. The elastic sealing cap 7 in the present embodiment comprises in total four openings 24 which are provided for leading through instruments. Thereby, two of these openings are provided with automatically closing valves 25 which are formed by conical sealing sections 25 which reach inwards into the funnel-like region 3 of the trocar sleeve 1 and which, with an existing pneumoperitoneum, automatically close on account of the excess pressure in the trocar sleeve 1 on removing the instrument 15 and may be opened again by way of introducing a instrument 15. Instead of these automatically closing elastic valves which are formed by the shape, one may also provide flap valves or mechanical shut-off devices, which close the respective opening after removal of the instrument. The pneumoperitoneum may be maintained or built up via the conduit 11.

The sealing caps 7 which are represented by way of the FIGS. 6 and 7 are designed as push-on caps. Advantageously, these may be fastened in a pivotable manner on the end section 4 of the trocar sleeve 1 by way of a joint, so that the cap may be pivoted, which has the advantage that the arrangement of the openings 24 is fixed with respect to the trocar sleeve 1 and therefore no longer needs to be aligned after the attachment.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A trocar sleeve (1) comprising a distal tubular section (2), a section (3) which connects to the distal tubular section at a proximal side and which is widened proximally, and at least one spiral (8) having a circular contour and arranged helically on a periphery of the distal tubular section (2), the distal tubular section (2) having a length and a width, the length extending parallel to a longitudinal axis of the distal tubular section (2) and extending perpendicularly to the width, wherein the distal tubular section (2) has a polygonal cross section extending perpendicularly to the longitudinal axis of the distal tubular section (2) and parallel to the width of the distal tubular section (2), the at least one spiral (8) extending radially outwardly beyond an outer periphery of the polygonal cross-section of the distal tubular section (2).

2. The trocar sleeve according to claim 1, wherein the at least one spiral (8) connects to an outer periphery of the distal tubular section (2) over an entire length of the at least one spiral in a distance-free manner.

3. The trocar sleeve according to claim 1, wherein the distal tubular section (2) comprises a rounded triangular cross section.

4. The trocar sleeve according to claim 1, wherein means (5, 6) for releasable attachment of sealing means (7) are provided on the proximal side, said sealing means sealing the trocar sleeve (1) on the proximal side to a outside and comprising at least one automatically closing or closable opening (24) for leading through an instrument (15).

5. The trocar sleeve according to claim 1, wherein an end section (19) connects on the proximal side to the widened section (3) and is provided with a peripheral bead (6), over which a sealing cap (7) engages.

6. The trocar sleeve according to claim 5, wherein a holding rod (10) connects on an outer side of the end section (19), the holding rod is bent upwardly and is guided proximally and parallel to a longitudinal axis of the trocar sleeve (1), a holding arm (13) which is arranged on the holding rod in an adjustable manner and is arranged for guiding and fixing an instrument (15) led through the trocar sleeve (1).

7. The trocar sleeve according to claim 1, wherein a trocar (17) is fastened in the trocar sleeve (1) and comprises a distal end section (19) which is tapered into a tip and whose outer contour corresponds to an inner cross section of the distal tubular section (2) and which is provided with at least one spiral (20) which connects to the at least one spiral (8) on the periphery of the distal tubular section (2) in a flush manner, when the trocar (17) is fixed in the trocar sleeve (1) in its correct position.

8. The trocar sleeve according to claim 7, wherein a distal end (8a) of the at least one spiral (8) on the periphery of the distal tubular section (2) is arranged distally displaced with respect to a proximal end (20a) of the spiral (20) of the trocar (17).

9. The trocar sleeve according to claim 7, wherein the trocar (17) comprises a rod (22) which connects on a proximal side to the distal end section (19), said rod having an end-side handle (23) which is dimensioned such that the handle (23) projects beyond the trocar sleeve (1) on the proximal side, when the trocar (17) is fixed in the trocar sleeve (1) in its correct position.

10. The trocar sleeve according to claim 1, wherein the section (3) is uniformly tapered from a distal end thereof to a proximal end thereof.

11. A trocar sleeve comprising a distal tubular section (2), a section (3) which connects to the distal tubular section at a proximal side and which is widened proximally, and at least one spiral (8) having a circular contour and arranged helically on a periphery of the distal tubular section (2), wherein the distal tubular section (2) has a rounded polygonal cross section,
wherein an end section (19) connects on the proximal side to the widened section (3) and is provided with a peripheral bead (6), over which a sealing cap (7) engages,
wherein a holding rod (10) connects on an outer side of the end section (19), the holding rod is bent upwardly and is guided proximally and parallel to a longitudinal axis of the trocar sleeve (1), wherein a holding arm (13) is arranged on the holding rod in an adjustable manner and is arranged for guiding and fixing an instrument (15) led through the trocar sleeve (1), and
wherein the holding rod (10) at least in sections is designed in a hollow manner, forms a conduit connection into an inside of the trocar sleeve (1) and comprises a conduit connection (11) which may be shut off.

12. A trocar sleeve comprising a distal tubular section (2), a section (3) which connects to the distal tubular section at a proximal side and which is widened proximally, and at least one spiral (8) having a circular contour and arranged helically on a periphery of the distal tubular section (2), wherein the distal tubular section (2) has a rounded polygonal cross section,
wherein a trocar (17) is fastened in the trocar sleeve (1) and comprises a distal end section (19) which is tapered into a tip and whose outer contour corresponds to an inner cross section of the distal tubular section (2) and which is provided with at least one spiral (20) which connects to the at least one spiral (8) on the periphery of the distal tubular section (2) in a flush manner, when the trocar (17) is fixed in the trocar sleeve (1) in its correct position,
wherein the trocar (17) comprises a rod (22) which connects on a proximal side to the distal end section (19), said rod having an end-side handle (23) which is dimensioned such that the handle (23) projects beyond the trocar sleeve (1) on the proximal side, when the trocar (17) is fixed in the trocar sleeve (1) in its correct position, and
wherein means for fixing the trocar (17) on the trocar sleeve (1) are provided on the handle (23) or on the rod (22), and a distally directed holding rod (16) is provided on the handle (23) and is fastened in a holding arm (13).

* * * * *